US011425901B2

(12) United States Patent
Zhao et al.

(10) Patent No.: US 11,425,901 B2
(45) Date of Patent: Aug. 30, 2022

(54) IN-VITRO CARDIOPULMONARY COMBINED PERFUSION SYSTEM AND PERFUSION METHOD

(71) Applicant: The First Affiliated Hospital, Sun Yat-sen University, Guangzhou (CN)

(72) Inventors: Qiang Zhao, Guangzhou (CN); Jinbo Huang, Guangzhou (CN); Yefu Li, Guangzhou (CN); Honghui Chen, Guangzhou (CN); Zhiyong Guo, Guangzhou (CN); Xiaoshun He, Guangzhou (CN)

(73) Assignee: THE FIRST AFFILIATED HOSPITAL, SUN YAT-SEN UNIVERSITY, Guangzhou (CN)

( * ) Notice: Subject to any disclaimer, the term of this patent is extended or adjusted under 35 U.S.C. 154(b) by 0 days.

(21) Appl. No.: 17/459,804

(22) Filed: Aug. 27, 2021

(65) Prior Publication Data
US 2022/0151224 A1 May 19, 2022

(30) Foreign Application Priority Data
Nov. 18, 2020 (CN) .......................... 202011295220.3

(51) Int. Cl.
*A01N 1/02* (2006.01)
*A61M 1/36* (2006.01)
*A61M 25/06* (2006.01)

(52) U.S. Cl.
CPC ......... *A01N 1/0247* (2013.01); *A01N 1/0242* (2013.01); *A01N 1/0284* (2013.01); *A01N 1/0289* (2013.01); *A61M 1/3666* (2013.01); *A61M 25/06* (2013.01)

(58) Field of Classification Search
CPC .. A01N 1/0247; A01N 1/0242; A01N 1/0284; A01N 1/0289; A01N 1/02; A01N 1/0205; A01N 1/0273; A01N 1/0263; A01N 1/021; A61M 1/3666; A61M 25/06
See application file for complete search history.

(56) References Cited

U.S. PATENT DOCUMENTS

| 2011/0136096 | A1* | 6/2011 | Hassanein | ......... | G01N 33/4925 435/1.2 |
| 2019/0059359 | A1* | 2/2019 | Potenziano | ........... | A61B 17/00 |

* cited by examiner

*Primary Examiner* — Michael L Hobbs
(74) *Attorney, Agent, or Firm* — D'Ambrosio & Menon, PLLC; Usha Menon

(57) ABSTRACT

Disclosed are an in-vitro cardiopulmonary combined perfusion system and perfusion method. The in-vitro cardiopulmonary combined perfusion system includes an organ cabin, a circulation cabin, a control cabin, a simple breathing cabin, a display and control panel, and a base. The organ cabin is connected with the circulation cabin, the control cabin and the simple breathing cabin. The control cabin is connected with the display and control panel. The organ cabin, the circulation cabin, the control cabin, the simple breathing cabin, and the display and control panel are mounted on the base.

8 Claims, 4 Drawing Sheets

IN-VITRO CARDIOPULMONARY COMBINED PERFUSION SYSTEM AND PERFUSION METHOD

CROSS-REFERENCE TO RELATED APPLICATIONS

This application is based on and claims the benefit of priority from Chinese Patent Application No. 202011295220.3, filed on Nov. 18, 2020, the entirety of which is incorporated by reference herein.

TECHNICAL FIELD

The present disclosure relates to the field of organ transplantation technologies, and more particularly, to an in-vitro cardiopulmonary combined perfusion system and perfusion method.

BACKGROUND

Organ transplantation is an effective measure to treat an end-stage organ disease. At present, there are still about 300,000 people waiting for organ transplantation, so that every donor is very precious. Therefore, it is very important to do a good job in perfusion preservation of the donor.

With the development of cardiopulmonary transplantation technology, more and more attention has been paid to the protection of a heart and a lung of the donor, and a preservation quality of the heart and the lung of the donor directly affects a survival rate of a patient after organ transplantation. At present, an organ preserving fluid is mainly used in low temperature soaking to preserve in-vitro heart and lung in clinical practice, which aims to reduce metabolism of the in-vitro heart and lung through a low temperature, reduce energy consumption of cells and accumulation of metabolic wastes, and reduce an injury of cardiopulmonary organs, thus prolonging an in-vitro preservation time of the in-vitro heart and lung. However, the low temperature preservation usually lasts for a few hours only, which cannot prevent death of cells, and meanwhile, a low temperature condition may also damage tissues and cells. In addition, after in-vitro organs preserved at a low temperature are transplanted to a receptor, blood supply needs to be restored, and at the moment, the organs inevitably go through an ischemia reperfusion injury.

There have been some research achievements in heart preservation or lung preservation, including CN201520313146.1, CN201811190296.2 and CN201810088427.X. However, there are no system and method for simultaneous cardiopulmonary combined perfusion preservation.

SUMMARY

The present disclosure aims to provide an in-vitro cardiopulmonary combined perfusion system and perfusion method. In-vitro organs are preserved by using an organ perfusion method, an ischemia reperfusion injury caused by low-temperature preservation is avoided, and a problem that in-vitro cardiopulmonary organs cannot be perfused and preserved at the same time is solved, and meanwhile, problems of lack of real anatomical organs in clinician training and lack of disease models in pathological research at present are also solved.

The above objective of the present disclosure is achieved by the following technical solutions.

An in-vitro cardiopulmonary combined perfusion system includes an organ cabin, a circulation cabin, a control cabin, a simple breathing cabin, a display and control panel, and a base, wherein the organ cabin is connected with the circulation cabin, the control cabin and the simple breathing cabin, the control cabin is connected with the display and control panel, and the organ cabin, the circulation cabin, the control cabin, the simple breathing cabin, and the display and control panel are mounted on the base.

Further, the organ cabin includes a trachea cannula orifice, an aorta cannula and an inferior vena cava cannula orifice, the aorta cannula and the inferior vena cava cannula orifice are respectively connected with the circulation cabin, and the trachea cannula orifice is connected with the simple breathing cabin.

Further, the organ cabin further includes an atomization nozzle, a water bath system, a cabin cover, an instrument jack, an inferior vena cava clip and an aorta cannula clip, the atomization nozzle is located on an inner side wall of the organ cabin, the water bath system is located at a bottom portion of the organ cabin and the cabin cover is located at an upper portion of the organ cabin, the instrument jack is mounted in the cabin cover, the inferior vena cava clip is mounted on a conduit of the inferior vena cava cannula orifice, and the aorta cannula clip is mounted on a conduit of the aorta cannula.

Further, a rapid vascular anastomotic stoma is mounted at an aorta cannula orifice and the inferior vena cava cannula orifice, the rapid vascular anastomotic stoma includes an inner cannula and an outer cannula, the inner cannula is mounted inside the outer cannula, a wall of the inner cannula is of a double-layer structure including an inner layer and an outer layer, a length of the inner layer of the double-layer structure is longer than that of the outer layer of the double-layer structure to form an outwardly convex end, a fine needle is placed in the double-layer structure, one end of the fine needle is connected with a stressed handle, the outer layer of the double-layer structure is provided with an assisting handle, and a total length of the fine needle is longer than that of the double-layer structure.

Further, the circulation cabin is located directly below the organ cabin, the circulation cabin includes a compliance chamber device, a blood bank, a leukocyte filter, a peristaltic pump and a thrombus filter, and the compliance chamber device is sequentially connected with the blood bank, the leukocyte filter, the peristaltic pump and the thrombus filter.

Further, the compliance chamber device includes a systolic and diastolic bag, a regulating chamber, a vascular resistance valve inlet, a vascular resistance valve outlet, a pressure valve inlet, a pressure valve outlet and a medium source, both ends of the systolic and diastolic bag are respectively provided with the vascular resistance valve inlet and the vascular resistance valve outlet, the systolic and diastolic bag is sleeved inside regulating chamber, the regulating chamber is respectively connected with the vascular resistance valve outlet, the pressure valve inlet and the pressure valve outlet, the medium source is connected with the pressure valve inlet, the systolic and diastolic bag is made of a stretchable flexible material, the regulating chamber is made of a hard material, the regulating chamber is filled with a compressible medium, the regulating chamber is internally provided with a pressure sensor, and a signal of the pressure sensor is processed by the control cabin and then outputted to the vascular resistance valve outlet and/or the pressure valve inlet and/or the pressure valve outlet.

Further, the control cabin includes a computer host, a training evaluation system, a video recording and storage system, and an instrument slot, the computer host is configured for receiving, processing and outputting a signal, the training evaluation system is configured for receiving data of an instrument operation for quantitative analysis and result output, the video recording and storage system is configured for receiving a signal of an external endoscope camera, recording the signal and feeding the signal back to the display and control panel, and the instrument slot is located on an outside wall of the control cabin.

Further, a simple breathing machine is placed in the simple breathing chamber, the control cabin is located on one side of the circulation cabin, and the simple breathing chamber is located at an upper portion of the control cabin and located on one side of the organ cabin.

Further, the cabin cover includes a left part and a right part which are of an arch structure as a whole, and an illuminating lamp is mounted on an inner surface of the cabin cover towards a cabin body.

An in-vitro cardiopulmonary combined perfusion method includes the following steps of:

S1: preparing a perfusion fluid: preparing an erythrocyte perfusion fluid of the same type as a perfused organ;

S2: starting a perfusion system: starting a water bath system, keeping a temperature of the perfusion fluid and a temperature of an organ cabin at 32° C. to 37° C., connecting an aorta cannula orifice with an inferior vena cava cannula orifice by an extension tube, and starting a peristaltic pump to run a machine;

S3: acquiring and loading an organ: cutting iliac veins on both sides of a donor or an experimental animal for standby, cutting a sternum to open a chest, then using two standby iliac veins to bridge with an inferior vena cava and an aorta respectively at a site where the inferior vena cava passes through a diaphragm, using one extension tube to connect the inferior vena cava cannula orifice with the bridged iliac vein, using the other extension tube to connect the aorta cannula orifice with the aorta, ligating left and right carotid arteries, left and right jugular veins, left and right subclavian arteries and left and right subclavian veins, then clipping the inferior vena cava and opening the bridged iliac vein, clipping the aorta and opening the bridged iliac vein at the same time, completely cutting off a heart and a lung through a thoracic entrance, a pleural cavity and a thoracic surface of the diaphragm, transferring the in-vitro heart and lung to the organ cabin, closing an inferior vena cava clip, an aorta cannula clip, the bridged iliac veins and the aorta at the same time, removing the two extension tubes, and quickly connecting the inferior vena cava with the inferior vena cava cannula orifice and connecting the aorta with the aorta cannula orifice through rapid vascular anastomotic stomas;

S4: running: after completing cannula connection, quickly releasing the inferior vena cava clip, the aorta cannula clip, the inferior vena cava and the aorta, restoring blood supply of the in-vitro heart and lung, after pumping blood for the in-vitro heart, allowing the perfusion fluid to flow into the circulation cabin through the aorta cannula orifice, allowing the perfusion fluid to enter the systolic and diastolic bag through a vascular resistance valve inlet, then allowing the perfusion fluid to flow out to a compliance chamber device through a vascular resistance valve outlet, then allowing the perfusion fluid to enter a blood bank, allowing the perfusion fluid in the blood bank to flow through a leukocyte filter to filter out leukocytes, then under the drive of the peristaltic pump, allowing the perfusion fluid to flow back to the inferior vena cava through the inferior vena cava cannula orifice, then allowing the perfusion fluid to flow back to a right atrium and a right ventricle, then perfusing bilateral in-vitro lungs through left and right pulmonary arteries, maintaining a respiratory movement of the lungs through a simple breathing machine, oxygenating erythrocytes in the perfusion fluid here and releasing carbon dioxide, then allowing the perfusion fluid to flow back into a left atrium through left and right pulmonary veins, and continuing to run; and S5: perfusing and preserving: mounting a cardiac pacemaker in the perfused organ, and monitoring a cardiac state in real time by the cardiac pacemaker and monitoring a coronary blood flow by a difference between an aortic diastolic pressure and a CVP; and using blood gas analysis on both sides of the inferior vena cava and the aorta to judge a functional state of the lungs, releasing 200 ml of perfusion fluid by an equivalent replacement method every 4 hours, and adding 200 ml of fresh perfusion fluid.

To sum up, the present disclosure has the beneficial effects as follows.

(1) The system is configured for in-vitro cardiopulmonary combined perfusion, which basically preserves normal anatomical structures of the heart and the lung. In terms of clinical teaching, the system can be used as a living organ training system. On one hand, cardiopulmonary combined perfusion basically preserves a normal anatomical structure of a thoracic cavity, and can accurately simulate bleeding, a respiratory movement of lungs, rhythmic beating of heart, etc., on the other hand, operation training can be broadcast and commented on in real time through a display screen, and meanwhile, objective indexes such as a bleeding volume, a trembling degree and an accuracy can also be recorded for evaluation, thus having a better simulated training effect. In terms of scientific research practice, an in-vitro cardiopulmonary perfusion platform not only provides a disease model at an organ level, but also retains an anatomical relationship between the heart and the lung, and is an organ platform for exploring an interaction mechanism between cardiopulmonary diseases. Compared with previous cell or animal models, a model of a diseased human body organ is closer to a whole disease state of a human body, for example, in tumor research, it is easier to simulate a high heterogeneity of the tumor of a human body and an internal environment of the tumor, which is more helpful for research of a pathophysiological mechanism of the cardiopulmonary diseases, research and development of drugs, etc.

(2) The perfusion is carried out with the perfusion fluid based on erythrocytes, interruption of blood flow of the in-vitro organ is minimized to prevent the ischemia reperfusion injury after transplanting the organ to a receptor, and in clinical practice, the perfusion is expected to be used in ischemia-free transplantation of the in-vitro heart and lung in the future, which will greatly reduce the ischemia reperfusion injury, improve a quality of cardiopulmonary transplantation, and improve prognosis of a patient undergoing cardiopulmonary transplantation.

(3) The device can intelligently maintain coronary blood flow and keep in-vitro beating of the heart, and whether sufficient and stable coronary blood flow of a nutrient vessel of the heart can be kept is one of the most important factor to determine whether the in-vitro heart can keep beating, while the coronary blood flow mainly depends on a difference between a diastolic pressure of an aortic root and a pressure of the right atrium. Therefore, the device mainly ensures sufficient and stable coronary blood flow by keeping the pressure difference between the aortic root and the right atrium stable, that is, by keeping the diastolic pressure of the aortic root and the pressure of the right atrium stable. In order to keep the diastolic pressure stable, the device is designed with a compliance chamber structure. In order to keep the pressure of the right atrium or the CVP stable, the device is designed with the peristaltic pump, the CVP is kept within a range of 5 cmH2O to 12 cmH2O through the peristaltic pump to ensure sufficient cardiopulmonary perfusion blood volume and judge a functional state of the in-vitro heart. When the CVP is too low, insufficient cardiopulmonary perfusion volume is prompted, at the moment, feedback regulation is carried out to improve a rotating speed of the peristaltic pump and increase the cardiopulmonary perfusion fluid volume. When the CVP is too high, a bad blood pumping function of the heart or an excessively high volume of fluid refluxed and perfused to the in-vitro heart and lung are prompted, at the moment, feedback regulation is carried out to reduce a rotating speed of the peristaltic pump and reduce the perfusion volume passing through an inferior vena cava reflux cannula line. Through the above design, the coronary blood volume can be intelligently kept to be sufficient and stable, thus ensuring the beating of the in-vitro heart.

(4) The device is designed with a miniature pacemaker, which has the following main functions: firstly, if cardiac arrest occurs during transfer of the in-vitro heart and lung to a mechanical perfusion system, and cardiac rebeating still fails after restoring blood supply of the in-vitro heart and lung, the pacemaker can make the heart rebeat; secondly, after a period of perfusion, when the heart stops beating or a cardiac beating function is weakened, temporary beating of the heart can be kept with the help of the pacemaker, which reduces a work applied by myocardial cells themselves, and is helpful to recovery of a cardiac function; and thirdly, when the in-vitro heart can beat autonomously, the pacemaker can play a role of monitoring a heart rate and a heart rhythm, which is helpful to judge the functional state of the in-vitro heart.

(5) The device is designed with the rapid vascular anastomotic stoma, which can quickly connect the inferior vena cava and the aorta of the in-vitro heart and lung with corresponding orifices. Compared with traditional knotting fixation, the device can greatly reduce a fixing time, shorten an ischemia time of the in-vitro organs as much as possible, and reduce the ischemia reperfusion injury after transplantation.

(6) The device is designed with the simple breathing machine, endotracheal intubation can be carried out on a main bronchus of the in-vitro lung, the respiratory movement of the in-vitro lung is kept by the breathing machine, which not only can fully simulate a normal state of human lungs and achieve a good effect in clinical operation training, but also can provide sufficient oxygen supply for circulating the perfusion fluid and keep a stable cardiopulmonary cell function.

(7) The water bath system is designed in the present disclosure, which keeps the temperature of the perfusion liquid and the temperature of the organ cabin at 32° C. to 37° C., thus solving a problem that a low temperature in a low-temperature static preservation method causes a damage to tissues and cells of the in-vitro organs.

(8) All conduit systems of the device are heparin coatings and thrombus filters, which can effectively prevent formation of thrombus in the conduit and filter the thrombus, thus keeping stable running of the machine.

(9) The device is designed with the leukocyte filter, which can effectively filter out leukocytes, etc., is helpful to reduce an immune response after transplantation, and improves prognosis of a patient undergoing transplantation.

BRIEF DESCRIPTION OF THE DRAWINGS

To make the objectives, the technical solutions, and the advantages of the present disclosure clearer, the present disclosure is further described in detail hereinafter with reference to the accompanying drawings.

Figure 1:
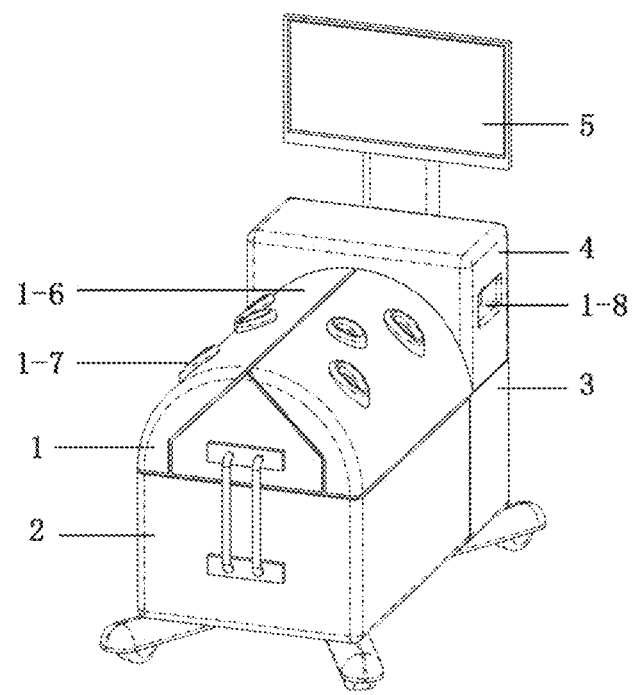
FIG. 1 is a schematic diagram of a structure of an in-vitro cardiopulmonary combined perfusion system of the present disclosure.

Specific reference numerals are as follow:

1 refers to organ cabin; 2 refers to circulation cabin; 3 refers to control cabin; 4 refers to simple breathing cabin; 5 refers to display and control panel; 6 refers to rapid anastomotic cannula; 1-1 refers to trachea cannula orifice; 1-2 refers to atomization nozzle; 1-3 refers to aorta cannula; 1-4 refers to inferior vena cava cannula orifice; 1-5 refers to water bath system; 1-6 refers to cabin cover; 1-7 refers to instrument jack; 1-8 instrument slot; 1-9 refers to inferior vena cava clip; 1-10 refers to aorta cannula clip; 2-1 refers to compliance chamber device; 2-2 refers to blood bank; 2-3 refers to leukocyte filter; 2-4 refers to peristaltic pump; 2-5 refers to thrombus filter; 6-1 refers to inner cannula; 6-2 refers to outer cannula; A refers to systolic and diastolic bag; B refers to regulating chamber; C refers to vascular resistance valve inlet; D refers to vascular resistance valve outlet; E refers to pressure valve inlet; F refers to pressure valve outlet; and G refers to medium source.

DETAILED DESCRIPTION

In order to illustrate the technical solutions in the embodiments of the present disclosure or in the existing technologies more clearly, the drawings and technical solutions used in the description of the embodiments or the existing technologies will be briefly described below. Obviously, the drawings in the following description are merely some embodiments recorded in the present disclosure. For those of ordinary skills in the art, other drawings may also be obtained based on these drawings without going through any creative work.

The present disclosure is further described hereinafter with reference to the accompanying drawings.

Figure 2:
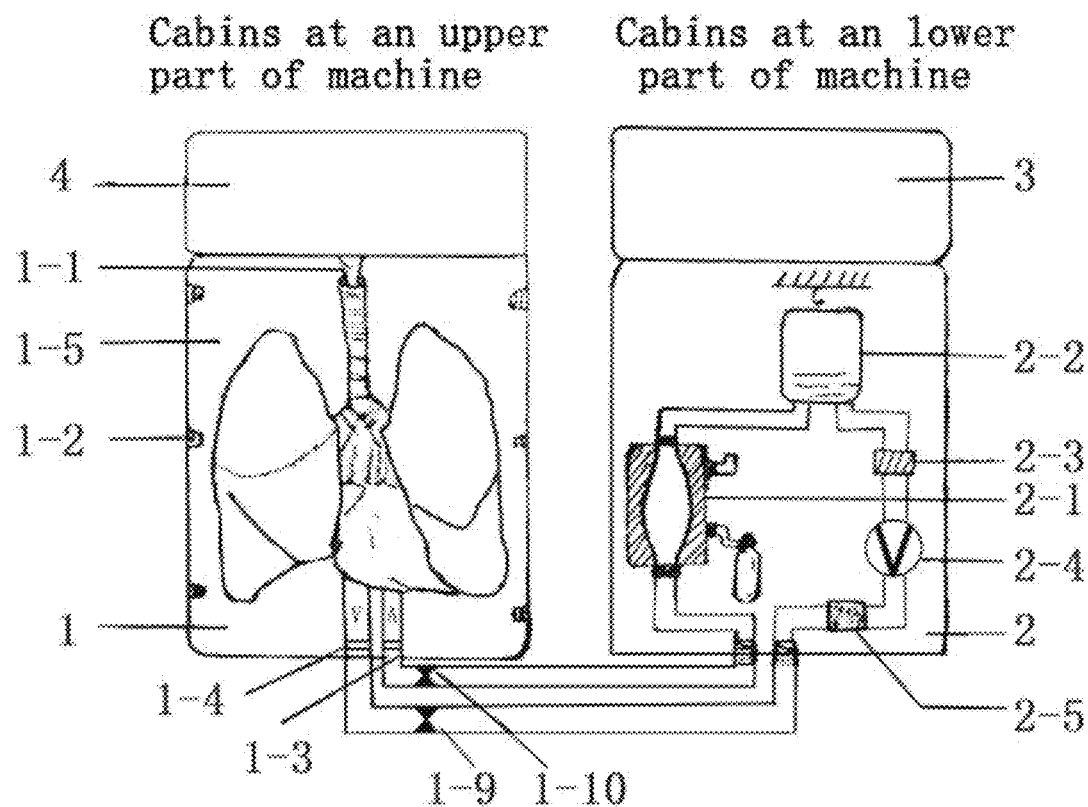
FIG. 2 is a principle diagram of the in-vitro cardiopulmonary combined perfusion system of the present disclosure.

As shown in FIG. 1 and FIG. 2, an in-vitro cardiopulmonary combined perfusion system aims to provide a normal physiological environment similar to a human body for in-vitro heart and lung at the same time, and intelligently keep long-term stability of the environment where the in-vitro heart and lung are located, which may be used for combined preservation of the in-vitro heart and lung at a normal temperature, cardiopulmonary endoscopic operation, and establishment of a human body diseased organ model. The device mainly includes an organ cabin 1, a circulation cabin 2 located below the organ cabin, a control cabin 3 located behind and below the organ cabin, a simple breathing machine cabin 4 behind the organ cabin, and a display and control panel 5.

Figure 3:
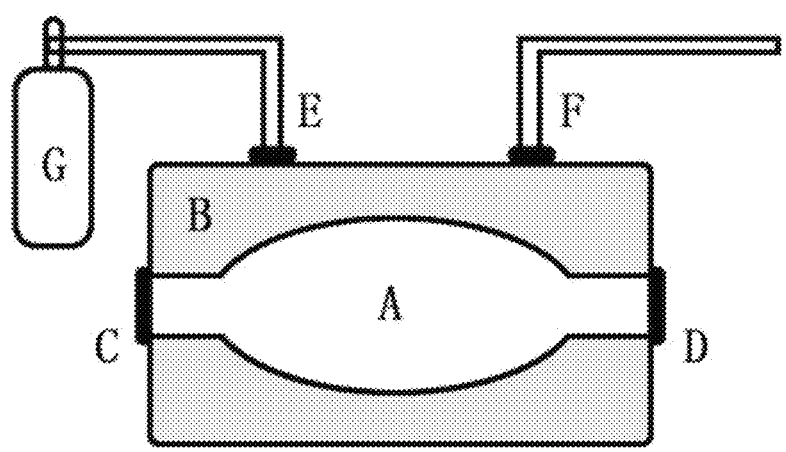
FIG. 3 is a schematic diagram of a structure of a compliance chamber device.
Figure 4:
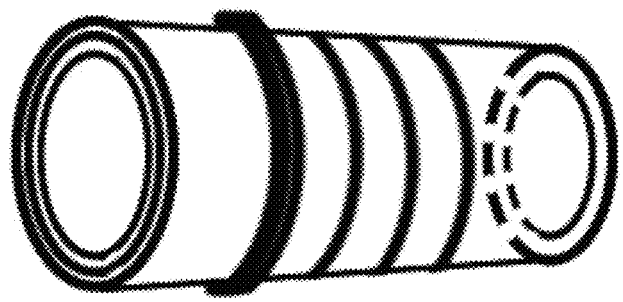
FIG. 4 is a schematic diagram of a structure of an inner cannula of a rapid anastomotic cannula.
Figure 5:
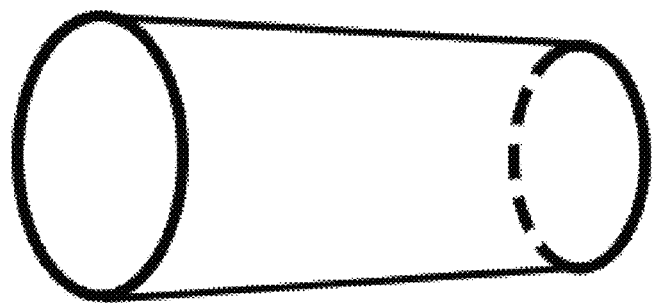
FIG. 5 is a schematic diagram of a structure of an outer cannula of the rapid anastomotic cannula.
Figure 6:
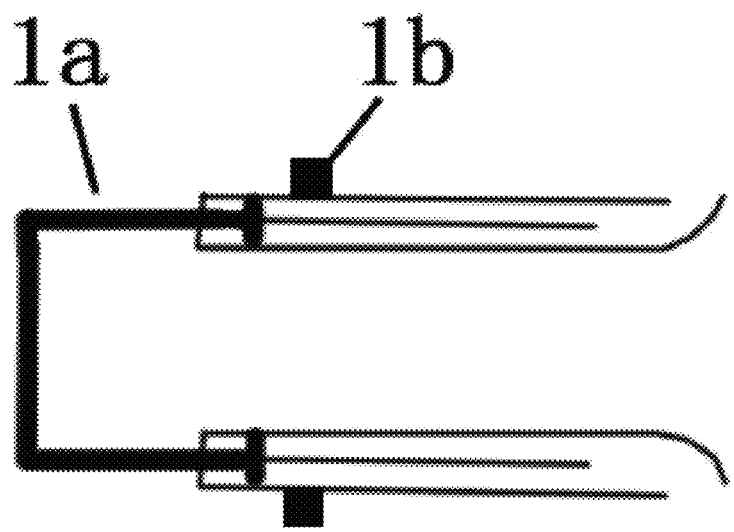
FIG. 6 is a cross-sectional view of the inner cannula of the rapid anastomotic cannula.
Figure 7:
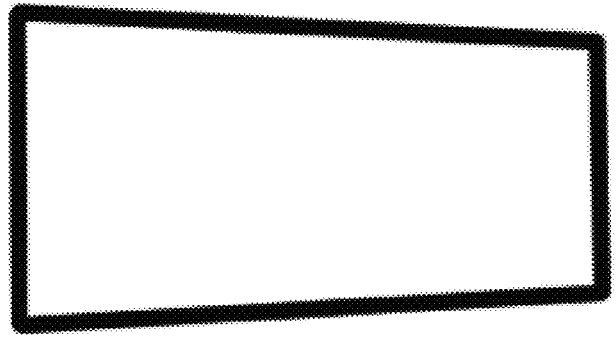
FIG. 7 is a cross-sectional view of the outer cannula of the rapid anastomotic cannula.

The organ cabin 1 includes in-vitro heart and lung, a trachea cannula orifice 1-1, an atomization nozzle 1-2, an aorta cannula orifice 1-3, an inferior vena cava cannula orifice 1-4, a water bath system 1-5, a double-door cabin cover 1-6 and an instrument jack 1-7 in the double-door cabin cover. Iliac veins on both sides of a donor or an experimental animal are cut for standby, a sternum is cut to open a chest, and then two standby iliac veins are used to bridge with an inferior vena cava and an aorta respectively at a site where the inferior vena cava passes through a diaphragm. One extension tube is used to connect the inferior vena cava cannula orifice 1-4 with the bridged iliac vein, the other extension tube is used to connect the aorta cannula orifice 1-3 with the aorta. Left and right carotid arteries, left and right jugular veins, left and right subclavian arteries and left and right subclavian veins are ligated, then the inferior vena cava is clipped and the bridged iliac vein is opened, and the aorta is clipped and the bridged iliac vein is opened at the same time. A heart and a lung are completely cut off through a thoracic entrance, a pleural cavity and a thoracic surface of the diaphragm, the in-vitro heart and lung are transferred to the organ cabin 1 as a whole, an inferior vena cava clip 1-9, an aorta cannula clip 1-10, the bridged iliac veins and the aorta are closed at the same time, and the two extension tubes are removed. The inferior vena cava cannula orifice 1-4 and the aorta cannula orifice 1-3 are both designed to be rapid vascular anastomotic stomas 6, which may quickly connect the inferior vena cava with the inferior vena cava cannula orifice 1-4 and connect the aorta with the aorta cannula orifice 1-3, thus shortening an ischemia time in an acquisition process of the in-vitro heart and lung as much as possible. As shown in FIG. 3, the rapid vascular anastomotic stoma 6 includes an anastomotic cannula 6-1 and an anastomotic cannula 6-2 which may be nested with each other, and the anastomotic cannulas are both columnar (a diameter difference between two ends of the cannulas is about 0.5 mm). A diameter of the anastomotic cannula 6-2 is a slightly larger than that of the anastomotic cannula 6-1, and the latter may be nested in the former. As shown in FIG. 4 to FIG. 7, a wall of the anastomotic cannula 6-1 is of an inner-outer double-layer structure with several fine needles arranged therein, a thicker end of the cannula is provided with a stressed handle 1a, which is connected with the fine needles and may push the fine needles in interlayers towards a thinner end of the cannula, inner and outer layers of the thinner end of the cannula have different lengths, and the inner layer exceeds the outer layer and bends towards the outer layer. When the fine needles in the interlayers are pushed to an elbow, the fine needles may tilt towards the outer layer, and the outer layer is designed with an assisting handle 1b. The anastomotic cannula 6-2 is of a single-layer structure, the inferior vena cava or the aorta is sleeved inside the anastomotic cannula 6-2 through the thinner end of the cannula, and the inferior vena cava or the aorta is clamped into an outside wall of the anastomotic cannula 6-1 together with the anastomotic cannula 6-2 as a whole, and then withdrawn from the anastomotic cannula 6-2. The inferior vena cava or the aorta remains embedded in the outside wall of the anastomotic cannula 6-1, the stressed handle 1a is pushed with the help of the assisting handle 1b, and after being contacted with an elbow of an inner side wall of the thinner end of the anastomotic cannula 6-1, the fine needles in the inner and outer interlayers tilt upwards and penetrate through the wall of the inferior vena cava or the aorta. At the moment, the anastomotic cannula 6-2 is sleeved into the anastomotic cannula 6-1, and the fine needles are flattened to quickly fix the inferior vena cava or the aorta. After fixing, the inferior vena cava clip 1-9, the aortic cannula clip 1-10, the inferior vena cava and the aorta are quickly released to restore blood supply of the in-vitro heart and lung. A conduit is placed in through inferior vena cava puncture and is extended into a right ventricle, and a miniature pacemaker is placed. When the heart beats normally, the pacemaker mainly plays a role of monitoring a heart rate and a heart rhythm. After being processed by the control cabin 3, the information may be displayed by a control panel and a display screen 5. After cardiac arrest, the pacemaker mainly plays a role of making the heart rebeat and keeping the heart beating. Meanwhile, the main bronchus of the in-vitro lung is connected with the simple breathing machine cabin 4 through the trachea cannula orifice 1-1, and a simple breathing machine is regulated to a suitable mode to keep a respiratory movement and oxygenation of the in-vitro lung. In addition, each side wall inside the organ cabin 1 is designed with the atomization nozzle 1-2 to keep the organ cabin 1 in a moist state and prevent the in-vitro heart and lung from being dry. A bottom portion of the organ cabin 1 is the water bath system 1-5, which keeps the in-vitro heart and lung at a suitable temperature usually set to be 32° C. to 37° C., and a top portion of the organ cabin 1 is designed with the double-door cabin cover 1-6. As shown in FIG. 1, the double-door cabin cover 1-6 may be opened from a middle to both sides and is in an arch shape, which simulates a thoracic structure of a human body. The cabin cover 1-6 is designed with the instrument jack 1-7, which may be used as a minimally invasive instrument or endoscope entrance for a minimally invasive operative instrument and the like to enter. The cabin cover is designed with an internal illuminating lamp. After pumping blood for the in-vitro heart, the blood flows into the circulation cabin 2 through the aorta cannula 1-3, the fluid in the circulation cabin 2 flows back to the inferior vena cava through the inferior vena cava cannula orifice 1-4, and then flows back to a right atrium and a right ventricle, then bilateral in-vitro lungs are perfused through left and right pulmonary arteries, and then the fluid flows back into a left atrium through left and right pulmonary veins, thus circularly simulating a normal blood circulation state in the human body.

The circulation cabin 2 is located directly below the organ cabin 1, and mainly includes a compliance chamber device 2-1, a blood bank 2-2, a leukocyte filter 2-3, a peristaltic pump 2-4 and a plug filter 2-5. After flowing into the circulation cabin 2 through the aorta cannula orifice 1-3, the perfusion fluid enters the compliance chamber device 2-1 first. As shown in FIG. 3, the compliance chamber device 2-1 is mainly used to keep a diastolic pressure and simulate a cardiac afterload, and keeping the diastolic pressure stable is helpful to keep a coronary blood flow of the heart, thus keeping the in-vitro heart beating continuously. The compliance chamber device mainly includes a systolic and diastolic bag A, a regulating chamber B, a vascular resistance valve inlet C, a vascular resistance valve outlet D, a pressure valve inlet E, a pressure valve outlet F and a medium source G. The blood pumped for the heart enters the systolic and diastolic bag A through the vascular resistance valve inlet C, and then flows out of the compliance chamber device through the vascular resistance valve outlet D. The vascular resistance valve inlet C and the vascular resistance valve outlet D mainly simulate vascular resistance by changing diameters of the valves, the diameter of the vascular resistance valve inlet C is close to that of an aortic root, and mainly simulates resistance of the aortic root, and the diameter of the vascular resistance valve outlet D is relatively small, and mainly simulates total resistance of surrounding blood vessels. The systolic and diastolic bag A is sleeved in the regulating chamber B, the systolic and diastolic bag A is made of a stretchable flexible material, and simulates vasoconstriction and vasodilatation, the regulating chamber B is made of a hard material, cannot be stretched, and is filled with a compressible medium, and meanwhile, a pressure sensor is designed, with a pressure information value transmitted to the pressure valve inlet E, the pressure valve outlet F and the vascular resistance valve outlet D. The pressure valve inlet E receives pressure information from the pressure sensor in the regulating chamber B, a lowest pressure value set for the pressure valve inlet E is the diastolic pressure, a lowest pressure value set for the vascular resistance valve outlet D is the diastolic pressure. In a case of diastole, the systolic and diastolic bag A is contracted, and the pressure in the regulating chamber B is reduced. When the pressure is reduced below the diastolic pressure set for the pressure valve inlet E and the vascular resistance valve outlet D, the pressure valve B is opened, the medium source G inputs a compressible medium into the regulating chamber B to increase the pressure in the regulating chamber B. Meanwhile, the diameter of the vascular resistance valve outlet D is reduced, and the pressure in the systolic and diastolic bag A is increased accordingly, which means that the aortic diastolic pressure may be kept above a certain set level, thus keeping the coronary blood flow. The pressure valve outlet F also receives the pressure information from the pressure sensor in the regulating chamber B, a highest value set for the pressure valve outlet F is the systolic pressure, a highest value set for the vascular resistance valve outlet D is the systolic pressure. In a case of systole, the systolic and diastolic bag A is relaxed, and the pressure in regulating chamber B is increased, when the pressure is increased above the systolic pressure set for the pressure valve outlet F, the pressure valve outlet F is opened, the medium in the regulating chamber B is discharged through the pressure valve outlet F to reduce the pressure in the regulating chamber B. Meanwhile, excessively high pressure information in the regulating chamber B may also be transmitted to the vascular resistance valve outlet D, the diameter of the vascular resistance valve is increased, and the pressure in the systolic and diastolic bag A is reduced accordingly, which means that the aortic diastolic pressure may be kept below a certain set level, thus preventing the aortic systolic pressure from being too high, preventing the afterload of the in-vitro heart from being too large, and keeping moderate energy consumption and oxygen consumption of the in-vitro heart. The perfusion fluid flows out of the compliance chamber device 2-1 through the vascular resistance valve outlet D, and then enters the blood bank 2-2. The blood bank 2-2 has two main functions, including coordinating a blood volume of arteries and veins, and simulating surrounding tissues to release oxygen. The perfusion fluid in the blood bank 2-2 flows through the leukocyte filter 2-3 to filter out leukocytes, and then under the drive of the peristaltic pump 2-4, the perfusion fluid passes through the thrombus filter 2-5, and then flows back to the inferior vena cava. A floating conduit is placed through an inferior vena cava reflux cannula line to the right atrium of the in-vitro heart or the right atrium where the inferior vena cava enters, and a pressure (i.e., a central venous pressure CVP) at the right atrium or the right atrium where the inferior vena cava enters is monitored. Main functions of monitoring the CVP are as follows: on one hand, one of the main influencing factors of the coronary blood flow is a difference between the diastolic pressure of the aortic root and the pressure of the right atrium, and by monitoring the CVP, combined with a monitoring value of the diastolic pressure, the coronary blood flow may be known in time; and on the other hand, a CVP monitoring value may be fed back to the peristaltic pump 2-4, and the CVP is kept within a range of 5 cmH2O to 12 cmH2O by the peristaltic pump, so as to ensure sufficient cardiopulmonary perfusion blood volume and judge a functional state of the in-vitro heart. When the CVP is too low, insufficient cardiopulmonary perfusion volume is prompted, and at the moment, feedback regulation is carried out to improve a rotating speed of the peristaltic pump and increase the cardiopulmonary perfusion fluid volume. When the CVP is too high, a bad blood pumping function of the heart or an excessively high volume of fluid refluxed and perfused to the in-vitro heart and lung are prompted, and at the moment, feedback regulation is carried out to reduce a rotating speed of the peristaltic pump and reduce the perfusion volume passing through the inferior vena cava reflux cannula line.

The simple breathing machine cabin 4 is located behind the organ cabin 2, which is mainly used for placing the simple breathing machine. The trachea cannula of the simple breathing machine enters the organ cabin 1 through the trachea cannula orifice 1-1 in the organ cabin 1. After the in-vitro heart and lung are completely acquired and fixed in the organ cabin, the trachea cannula may be inserted and fixed into the main bronchus of the in-vitro lung, and the breathing machine is regulated to a suitable mode to preserve a normal respiratory movement of the in-vitro lung. The perfusion fluid is extracted from the right atrium where the inferior vena cava enters and the aorta regularly for blood gas analysis, and a functional state of the in-vitro lung is analyzed by comparing indexes such as an oxygen saturation, an oxygen partial pressure and a carbon dioxide partial pressure of the two sites.

The control cabin 3 is mainly an information processing center, which is a processing center of regulatory signals of the device. The control cabin 3 is equipped with a computer host, which has a basic database function, and may record basic information of an operator and information collected by the sensors. Recorded index information usually includes the oxygen saturation, the oxygen partial pressure, the carbon dioxide partial pressure, the heart rate, the heart rhythm, the aortic systolic pressure, the aortic diastolic pressure, the central venous pressure, the pump speed and other indexes of monitoring points, and is displayed by the display and control panel 5. A training evaluation system is provided, which is connected with operating instruments such as an ultrasonic scalpel, an endoscope, an aspirator, etc., and may collect objective indicators such as a bleeding volume, a trembling degree and an accuracy for quantitative evaluation. A video recording and storage system is provided, which is connected with a camera of the endoscope, may be used to record an operation video, and broadcasts an operation training process in real time through the external display and control panel 5. The four cabins above are assembled and then fixed on a base 7, and the base 7 is designed with a lifting column for supporting, moving and lifting the whole device. A height of an operating platform may be regulated according to different lifting operations of an operator. An instrument slot 1-8 is mounted on an outer wall of the control cabin.

A perfusion method is as follows.

1. Preparation of perfusion fluid: the device mainly uses the perfusion fluid prepared by imitating blood to perfuse and preserve the in-vitro heart and lung. A main ingredient of the perfusion fluid is erythrocytes of the same type as a perfused organ, and the erythrocytes mainly play a role of carrying oxygen. Perfusion and preservation of the in-vitro organs with the perfusion fluid using the erythrocytes as the main ingredients is helpful to provide sufficient oxygen for the in-vitro organs. Other ingredients mainly simulate a blood environment suitable for survival of the erythrocytes, and mainly include a colloid fluid (simulating a function of albumin, etc., and keeping a colloid osmotic pressure of the perfusion fluid, so as to balance an osmotic pressure inside and outside blood vessels of the in-vitro organs and prevent tissue edema of the in-vitro organs), Na, Ca and Mg plasmas (keeping a crystalloid osmotic pressure of the perfusion fluid, so as to prevent cellular edema of the in-vitro organs, hemolysis of the erythrocytes, etc.), an antibiotic, a hormone, a trace element, an amino acid, an alkali, heparin, etc. In the preparation process, concentrated erythrocytes of the same blood type as the in-vitro organs are diluted to an appropriate proportion.

2. Preheating and standby of mechanical perfusion system: the water bath system is started, a temperature of the perfusion fluid and a temperature of the organ cabin 1 are kept at 32° C. to 37° C., the aorta cannula orifice 1-3 is connected with the inferior vena cava cannula orifice 1-4 by an extension tube, and the peristaltic pump is started to run a perfusion passage.

3. Acquisition and loading of organs: iliac veins on both sides of a donor or an experimental animal are cut for standby, a sternum is cut to open a chest, and then two standby iliac veins are used to bridge with the inferior vena cava and the aorta respectively at a site where the inferior vena cava passes through a diaphragm. One extension tube is used to connect the inferior vena cava cannula orifice 1-4 with the bridged iliac vein, the other extension tube is used to connect the aorta cannula orifice 1-3 with the aorta. Left and right carotid arteries, left and right jugular veins, left and right subclavian arteries and left and right subclavian veins are ligated, then the inferior vena cava is clipped and the bridged iliac vein is opened, and the aorta is clipped and the bridged iliac vein is opened at the same time. The heart and the lung are completely cut off through a thoracic entrance, a pleural cavity and a thoracic surface of the diaphragm, the in-vitro heart and lung are transferred to the organ cabin 1 as a whole, the inferior vena cava cannula orifice clip 1-9, the aorta cannula orifice clip 1-10, the bridged iliac veins and the aorta are closed at the same time, and the two extension tubes are removed. The inferior vena cava cannula orifice 1-4 and the aorta cannula orifice 1-3 are both designed to be the rapid vascular anastomotic stomas 6, which may quickly connect the inferior vena cava with the inferior vena cava cannula orifice 1-4 and connect the aorta with the aorta cannula orifice 1-3, thus shortening an ischemia time in an acquisition process of the in-vitro heart and lung as much as possible.

3. Running: after connecting the cannulas, the inferior vena cava cannula orifice clip 1-9, the aortic cannula orifice clip 1-10, the inferior vena cava and the aorta are quickly released to restore blood supply of the in-vitro heart and lung. If cardiac arrest occurs, the pacemaker may make the heart rebeat. After pumping blood for the in-vitro heart, the perfusion fluid flows into the circulation cabin 2 through the aorta cannula orifice 1-3, and in the circulation cabin 2, the perfusion fluid enters the systolic and diastolic bag A through the vascular resistance valve C, then flows out to the compliance chamber device through the vascular resistance valve D, and then enters the blood bank 2-2. The perfusion fluid in the blood bank 2-2 flows through the leukocyte filter 2-3 to filter out leukocytes, and then under the drive of the peristaltic pump, the perfusion fluid in the circulation cabin 2 flows back to the inferior vena cava through the inferior vena cava cannula orifice 1-4, then flows back to a right atrium and a right ventricle, and then perfused to bilateral in-vitro lungs through left and right pulmonary arteries. A respiratory movement of the lungs is kept through the simple breathing machine, erythrocytes in the perfusion fluid are oxygenated here and carbon dioxide is released, and then the perfusion fluid flows back into a left atrium through left and right pulmonary veins, thus circularly simulating a normal blood circulation state in the human body.

4. Perfusion and preservation: the cardiac state is monitored in real time by the pacemaker and the coronary blood flow is monitored by a difference between the aortic diastolic pressure and the CVP, so that the heart is kept to beat and preserved; and blood gas analysis on both sides of the inferior vena cava and the aorta are used to judge a functional state of the lung. 200 ml of perfusion fluid is released by an equivalent replacement method every 4 hours, and 200 ml of fresh perfusion fluid is added.

The foregoing is only the specific implementations of the present disclosure, but the scope of protection of the present disclosure is not limited thereto. Any changes or substitutions conceived without going through creative works should be included in the scope of protection of the present disclosure. Therefore, the scope of protection of the present disclosure should be subject to the scope of protection defined in the claims.

What is claimed is:

1. An in-vitro cardiopulmonary combined perfusion system, comprising an organ cabin, a circulation cabin, a control cabin, a simple breathing cabin, a display and control panel, and a base, wherein the organ cabin is connected with the circulation cabin, the control cabin and the simple breathing cabin, the control cabin is connected with the display and control panel, and the organ cabin, the circulation cabin, the control cabin, the simple breathing cabin, and the display and control panel are mounted on the base, the circulation cabin is located directly below the organ cabin, the circulation cabin comprises a compliance chamber device, a blood bank, a leukocyte filter, a peristaltic pump and a thrombus filter, and the compliance chamber device is sequentially connected with the blood bank, the leukocyte filter, the peristaltic pump and the thrombus filter.

2. The in-vitro cardiopulmonary combined perfusion system of claim 1, wherein, the organ cabin comprises a trachea cannula orifice, an aorta cannula and an inferior vena cava cannula orifice, the aorta cannula and the inferior vena cava cannula orifice are respectively connected with the circulation cabin, and the trachea cannula orifice is connected with the simple breathing cabin.

3. The in-vitro cardiopulmonary combined perfusion system of claim 2, wherein, the organ cabin further comprises an atomization nozzle, a water bath system, a cabin cover, an instrument jack, an inferior vena cava clip and an aorta cannula clip, the atomization nozzle is located on an inner side wall of the organ cabin, the water bath system is located at a bottom portion of the organ cabin and the cabin cover is located at an upper portion of the organ cabin, the instrument jack is mounted in the cabin cover, the inferior vena cava clip is mounted on a conduit of the inferior vena cava cannula orifice, and the aorta cannula clip is mounted on a conduit of the aorta cannula.

4. The in-vitro cardiopulmonary combined perfusion system of claim 3, wherein, a rapid vascular anastomotic stoma is mounted at an aorta cannula orifice and the inferior vena cava cannula orifice, the rapid vascular anastomotic stoma comprises an inner cannula and an outer cannula, the inner cannula is mounted inside the outer cannula, a wall of the inner cannula is of a double-layer structure comprising an inner layer and an outer layer, a length of the inner layer of the double-layer structure is longer than a length of the outer layer of the double-layer structure to form an outwardly convex end, a fine needle is placed in the double-layer structure, one end of the fine needle is connected with a stressed handle, the outer layer of the double-layer structure is provided with an assisting handle, and a total length of the fine needle is longer than a length of the double-layer structure.

5. The in-vitro cardiopulmonary combined perfusion system of claim 1, wherein, the compliance chamber device comprises a systolic and diastolic bag, a regulating chamber, a vascular resistance valve inlet, a vascular resistance valve outlet, a pressure valve inlet, a pressure valve outlet and a medium source, both ends of the systolic and diastolic bag are respectively provided with the vascular resistance valve inlet and the vascular resistance valve outlet, the systolic and diastolic bag is sleeved inside regulating chamber, the regulating chamber is respectively connected with the pressure valve inlet and the pressure valve outlet, the medium source is connected with the pressure valve inlet, the systolic and diastolic bag is made of a stretchable flexible material, the regulating chamber is made of a hard material, the regulating chamber is filled with a compressible medium, the regulating chamber is internally provided with a pressure sensor, and a signal of the pressure sensor is processed by the control cabin and then outputted to the vascular resistance valve outlet and/or the pressure valve inlet and/or the pressure valve outlet.

6. The in-vitro cardiopulmonary combined perfusion system of claim 1, wherein, the control cabin comprises a computer host, a training evaluation system, a video recording and storage system, and an instrument slot, the computer host is configured for receiving, processing and outputting a signal, the training evaluation system is configured for receiving data of an instrument operation for quantitative analysis and result output, the video recording and storage system is configured for receiving a signal of an external endoscope camera, recording the signal and feeding the signal to the display and control panel, and the instrument slot is located on a sidewall of the control cabin.

7. The in-vitro cardiopulmonary combined perfusion system of claim 1, wherein, a simple breathing machine is placed in the simple breathing chamber, the control cabin is located on one side of the circulation cabin, and the simple breathing chamber is located at an upper portion of the control cabin and located on one side of the organ cabin.

8. The in-vitro cardiopulmonary combined perfusion system of claim 3, wherein, the cabin cover comprises a left part and a right part which are of an arch structure as a whole, and an illuminating lamp is mounted on an inner surface of the cabin cover towards a cabin body.

* * * * *